(12) United States Patent
Cho et al.

(10) Patent No.: US 10,818,045 B2
(45) Date of Patent: Oct. 27, 2020

(54) MEDICAL IMAGING APPARATUS AND METHOD OF PROCESSING MEDICAL IMAGE

(71) Applicant: Samsung Electronics Co., Ltd., Gyeonggi-do (KR)

(72) Inventors: Min-kook Cho, Hwaseong-si (KR); Eung-jun Youn, Suwon-si (KR); Nam-woo Kim, Yongin-si (KR); Chang-lae Lee, Seoul (KR); Yu-na Choi, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 115 days.

(21) Appl. No.: 15/799,893

(22) Filed: Oct. 31, 2017

(65) Prior Publication Data
US 2018/0122108 A1 May 3, 2018

(30) Foreign Application Priority Data
Oct. 31, 2016 (KR) .................. 10-2016-0143423

(51) Int. Cl.
*G06T 11/00* (2006.01)
*G06T 5/50* (2006.01)
(Continued)

(52) U.S. Cl.
CPC .............. *G06T 11/005* (2013.01); *A61B 6/03* (2013.01); *A61B 6/461* (2013.01); *A61B 6/5205* (2013.01);
(Continued)

(58) Field of Classification Search
CPC ..... G06T 2211/408; G06T 2207/20221; A61B 6/482
See application file for complete search history.

(56) References Cited

U.S. PATENT DOCUMENTS 4,541,106 A * 9/1985 Belanger .................. H05G 1/44
378/118
4,792,900 A * 12/1988 Sones .................. A61B 6/4241
378/98.9
(Continued)

FOREIGN PATENT DOCUMENTS

| JP | 2008086543 A | 4/2008 |
| JP | 2014210180 A | 4/2016 |

(Continued)

OTHER PUBLICATIONS

European Patent Office, "European Search Report," European Application No. EP 17 19 8864, dated Mar. 6, 2018, 9 pages.

*Primary Examiner* — Gandhi Thirugnanam

(57) ABSTRACT

Various embodiments of this disclosure provide a medical imaging apparatus and a method of processing a medical image. The medical imaging apparatus includes a data obtainer configured to obtain raw data generated by performing a tomography scan on an object. The medical imaging apparatus also includes a processor configured to obtain, from the raw data, a plurality of pieces of monochromatic image data respectively corresponding to a plurality of energy levels. The processor is also configured to receive an external input that sets a combination of weights respectively applied to the plurality of pieces of monochromatic image data. The processor is also configured to generate a synthetic image by applying the combination of the weights to the plurality of pieces of monochromatic image data. The medical imaging apparatus also includes a display configured to display the generated synthetic image.

15 Claims, 13 Drawing Sheets

(51) Int. Cl.
*A61B 6/03* (2006.01)
*A61B 6/00* (2006.01)
*G06F 3/0484* (2013.01)
*G06F 3/0488* (2013.01)

(52) U.S. Cl.
CPC .............. *G06T 5/50* (2013.01); *G06T 11/008* (2013.01); *G06F 3/04842* (2013.01); *G06F 3/04845* (2013.01); *G06F 3/04883* (2013.01); *G06T 2200/24* (2013.01); *G06T 2207/10081* (2013.01); *G06T 2207/20092* (2013.01); *G06T 2207/20221* (2013.01); *G06T 2210/41* (2013.01); *G06T 2211/408* (2013.01)

(56) References Cited

U.S. PATENT DOCUMENTS

| | | | | |
|---|---|---|---|---|
| 5,115,394 A * | 5/1992 | Walters | G06T 11/006 | 378/4 |
| 5,931,780 A * | 8/1999 | Giger | A61B 6/482 | 600/407 |
| 6,240,201 B1 * | 5/2001 | Xu | G06T 7/0012 | 382/128 |
| 6,683,934 B1 * | 1/2004 | Zhao | A61B 6/032 | 378/37 |
| 6,760,611 B1 * | 7/2004 | Watanabe | G01R 33/5601 | 324/307 |
| 8,115,784 B2 | 2/2012 | Licato et al. | | |
| 8,184,877 B2 * | 5/2012 | VanMetter | G06T 11/008 | 378/98.9 |
| 8,761,479 B2 | 6/2014 | Avinash et al. | | |
| 10,275,883 B2 * | 4/2019 | Ihara | G06K 9/00973 | |
| 2001/0053240 A1 * | 12/2001 | Oosawa | G06K 9/6203 | 382/128 |
| 2003/0147497 A1 * | 8/2003 | Avinash | A61B 6/405 | 378/98.9 |
| 2006/0109949 A1 * | 5/2006 | Tkaczyk | A61B 6/032 | 378/4 |
| 2007/0014480 A1 * | 1/2007 | Sirohey | A61B 6/482 | 382/240 |
| 2007/0165920 A1 * | 7/2007 | Gering | A61B 5/055 | 382/128 |
| 2008/0192898 A1 * | 8/2008 | VanMetter | G06T 11/008 | 378/98.9 |
| 2009/0010380 A1 * | 1/2009 | Gotoh | A61B 6/032 | 378/5 |
| 2009/0052612 A1 * | 2/2009 | Wu | A61B 6/032 | 378/5 |
| 2009/0135994 A1 * | 5/2009 | Yu | A61B 6/032 | 378/5 |
| 2009/0297014 A1 * | 12/2009 | Nelms | G06F 19/321 | 382/132 |
| 2010/0135565 A1 * | 6/2010 | Thomsen | G06T 11/006 | 382/132 |
| 2010/0189212 A1 * | 7/2010 | Zou | G06T 11/005 | 378/5 |
| 2011/0243404 A1 * | 10/2011 | Li | G06T 11/008 | 382/128 |
| 2013/0142412 A1 * | 6/2013 | Oh | A61B 6/4241 | 382/132 |
| 2014/0140479 A1 * | 5/2014 | Wang | A61B 6/482 | 378/62 |
| 2016/0022243 A1 | 1/2016 | Nakai et al. | | |
| 2016/0070008 A1 | 3/2016 | Cao et al. | | |
| 2016/0106386 A1 * | 4/2016 | Fan | A61B 6/482 | 378/5 |
| 2016/0135774 A1 * | 5/2016 | Ono | A61B 6/5205 | 378/5 |
| 2018/0122108 A1 * | 5/2018 | Cho | A61B 6/03 | |
| 2019/0236763 A1 * | 8/2019 | Chan | G06T 5/50 | |

FOREIGN PATENT DOCUMENTS

| | | |
|---|---|---|
| JP | 2016055164 A | 4/2016 |
| WO | 2014176328 A1 | 10/2014 |
| WO | 2016093917 A1 | 6/2016 |

* cited by examiner

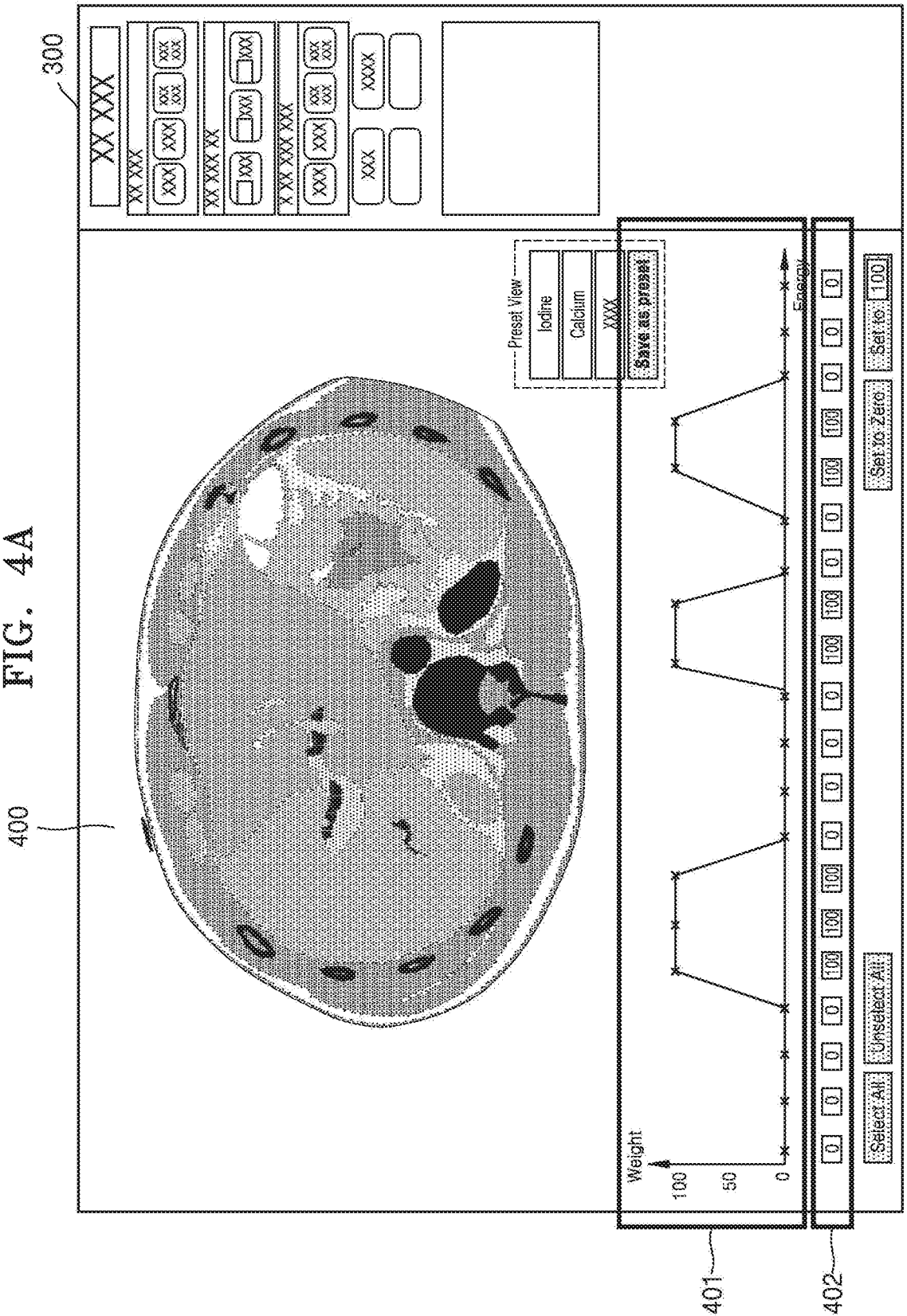

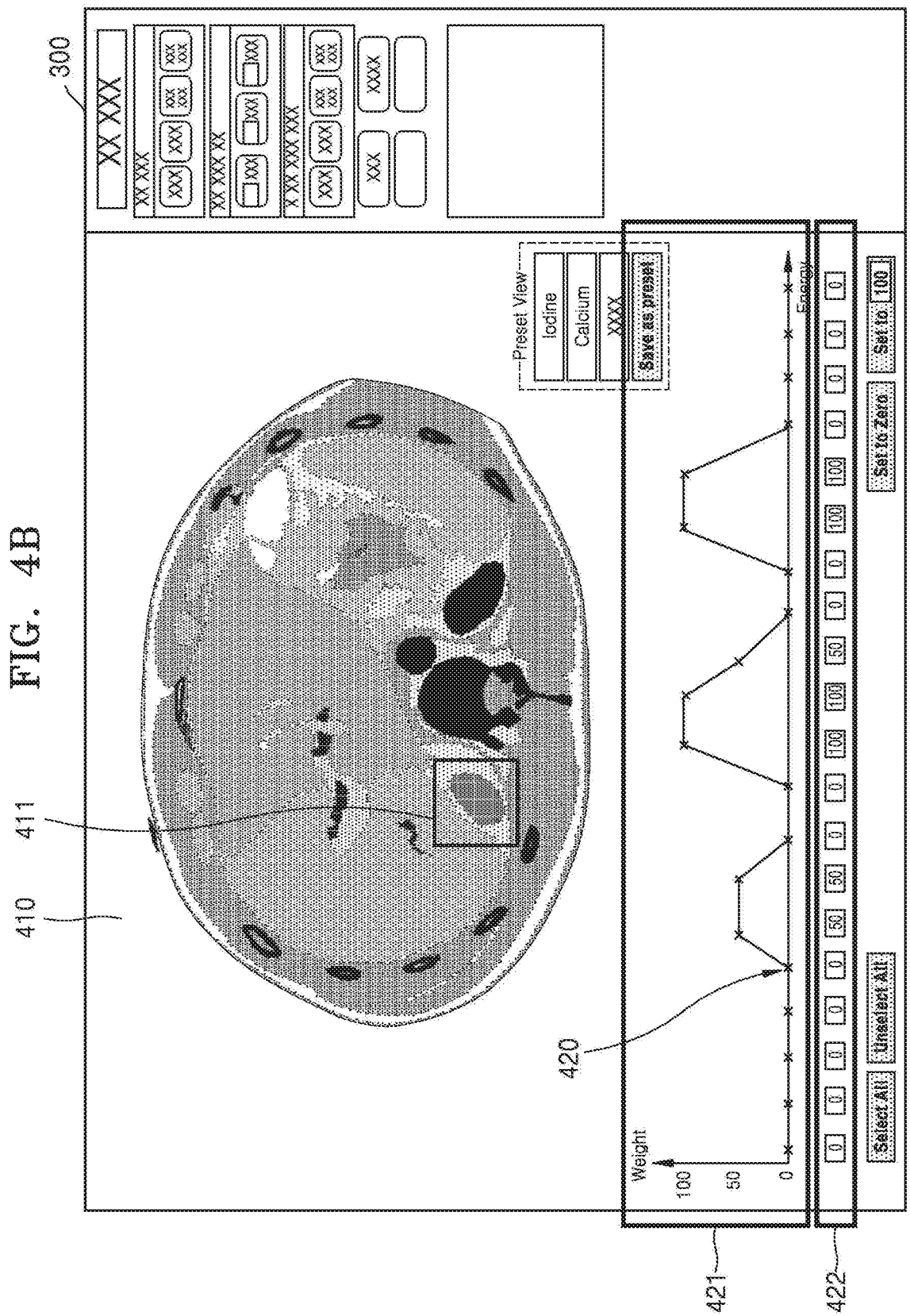

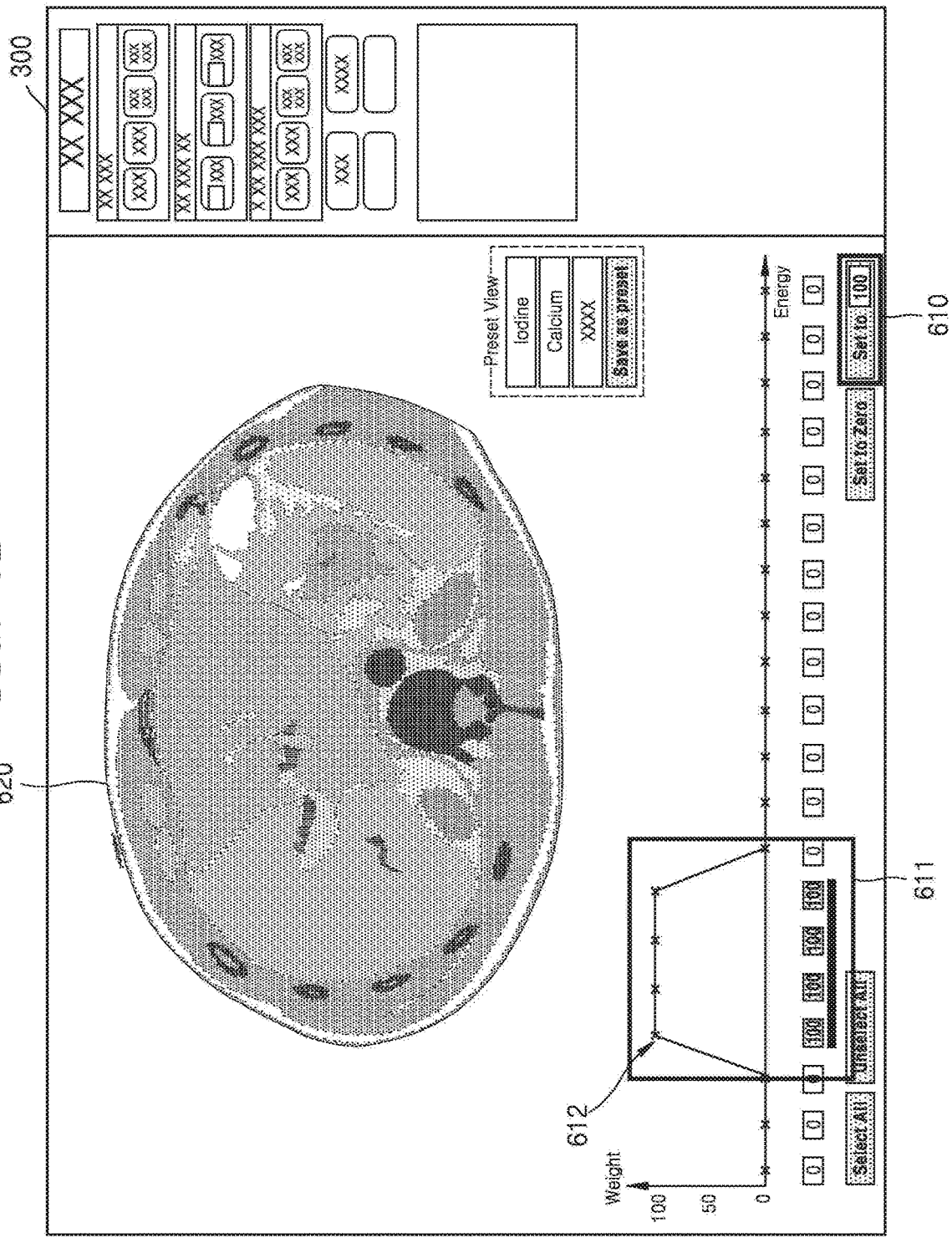

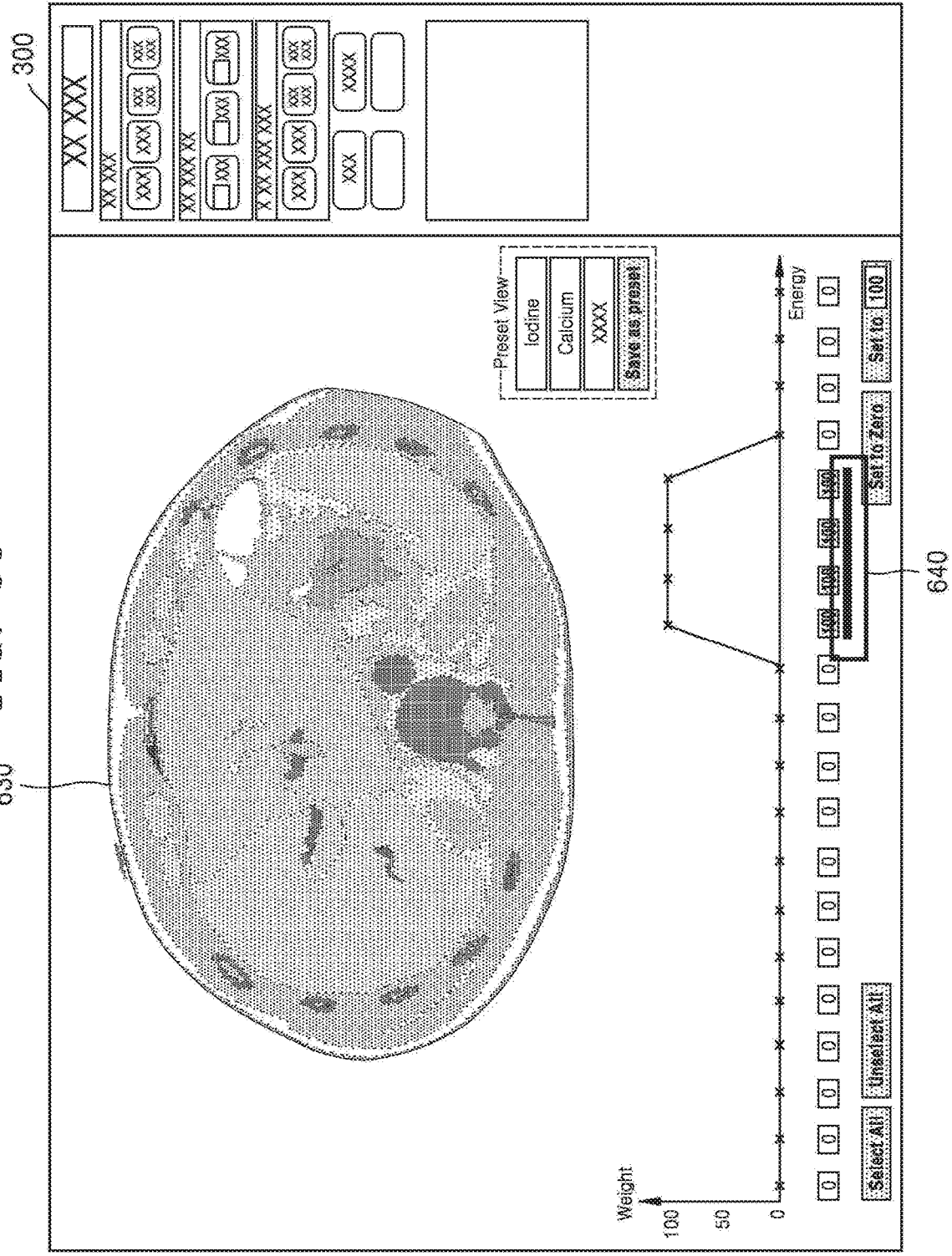

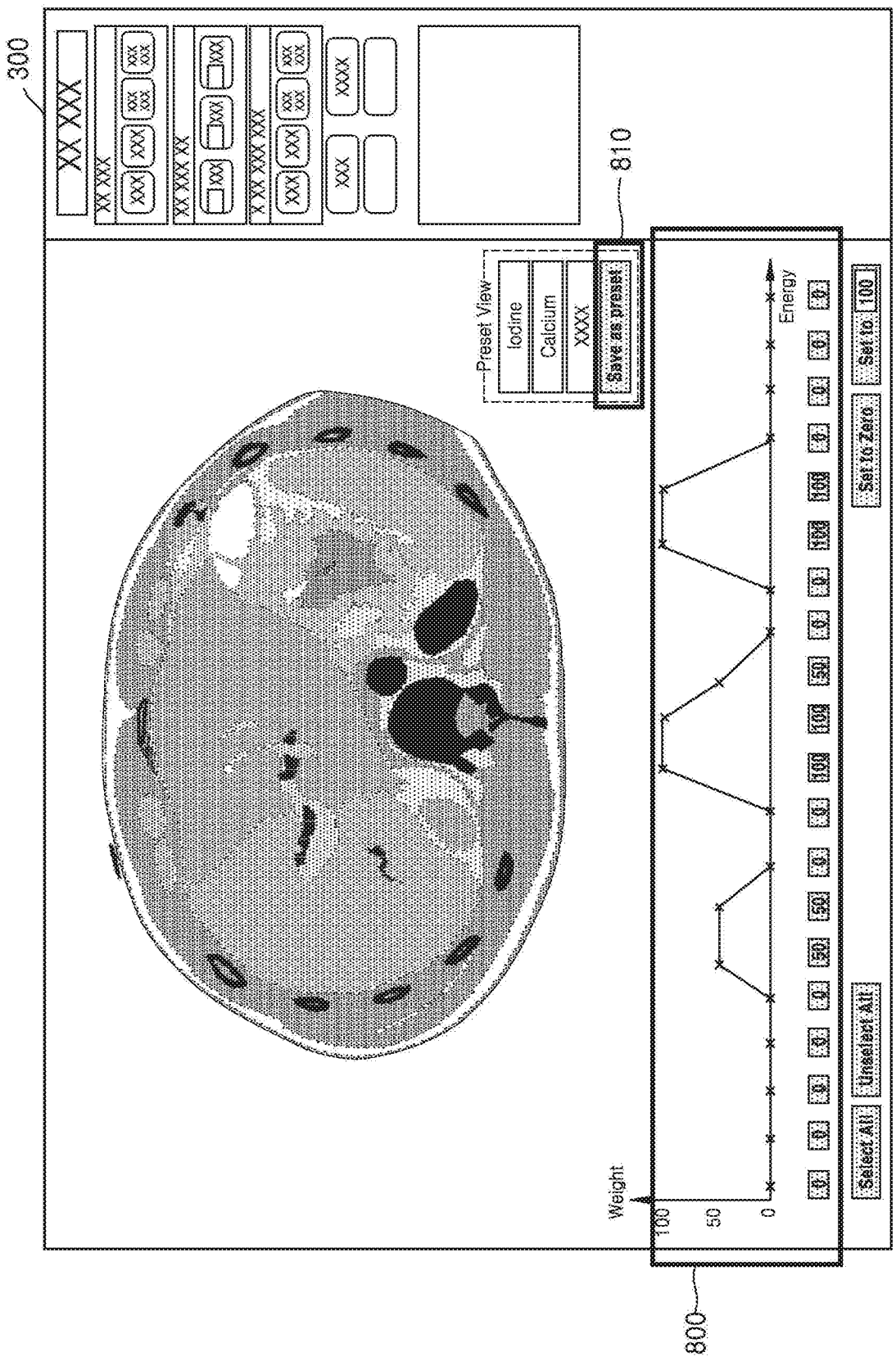

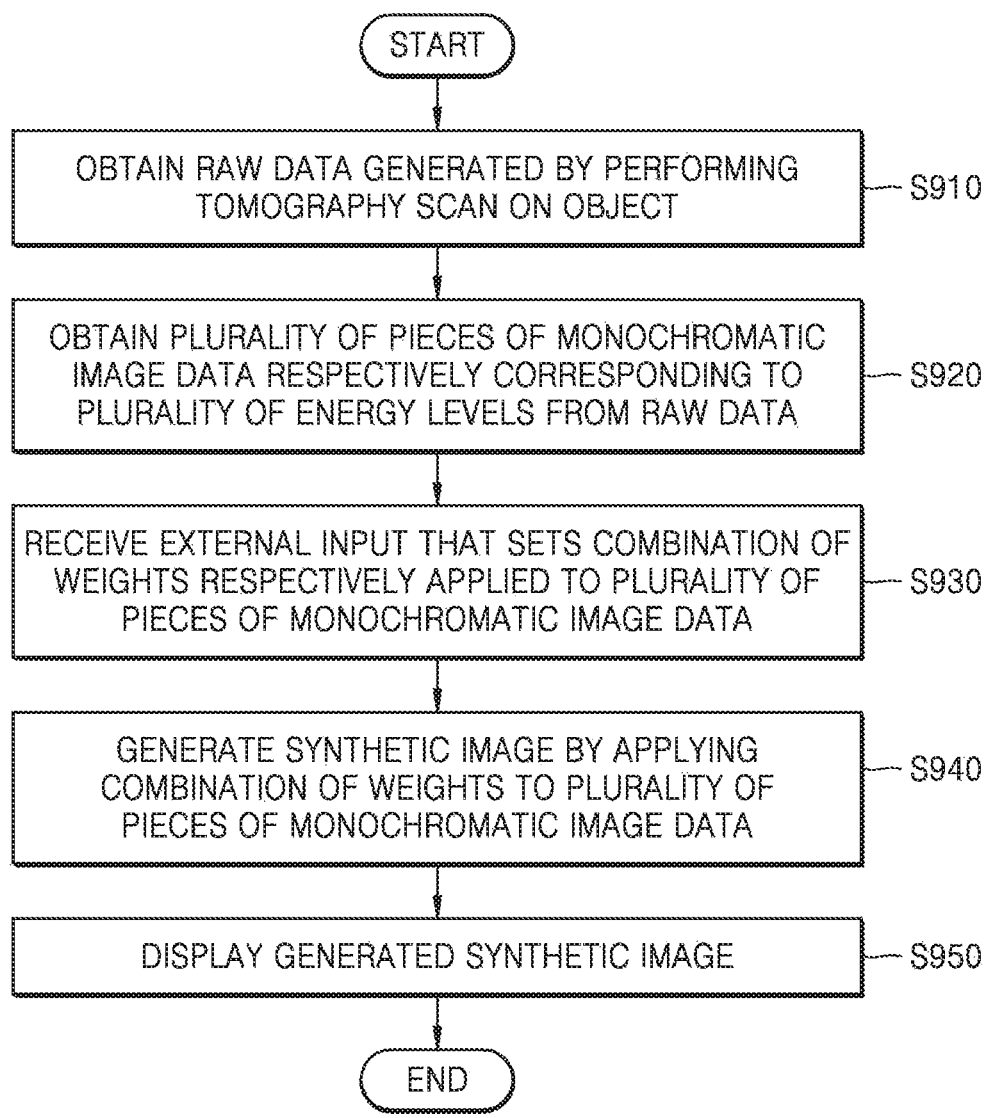

MEDICAL IMAGING APPARATUS AND METHOD OF PROCESSING MEDICAL IMAGE

CROSS-REFERENCE TO RELATED APPLICATION AND CLAIM OF PRIORITY

This application is related to and claims priority to Korean Patent Application No. 10-2016-0143423 filed on Oct. 31, 2016, the contents of which are incorporated herein by reference.

TECHNICAL FIELD

The present disclosure relates to medical imaging apparatuses, methods of processing medical images, and computer-readable recording media having recorded thereon computer program code for executing the methods.

BACKGROUND

Medical imaging apparatuses are used to obtain images of internal structures of objects. Medical imaging apparatuses that are non-invasive testing apparatuses capture and process images of structural details, internal tissues, and the flow of fluids in objects and provide the images to users. The users, who are, for example, medical doctors, may diagnose health states and diseases of patients by using medical images output from the medical imaging apparatuses. Accordingly, in order to precisely diagnose diseases, methods of obtaining medical images which may clearly distinguish different materials existing in objects are required.

SUMMARY

To address the above-discussed deficiencies, it is a primary object to provide various synthetic images by respectively applying weights to a plurality of pieces of monochromatic image data.

Also, objectives of embodiments are to enable users to easily check lesions or materials to be observed by users by generating synthetic images by applying various combinations of weights.

Additional aspects will be set forth in part in the description which follows and, in part, will be apparent from the description, or may be learned by practice of the presented embodiments.

According to an aspect of an embodiment, a medical imaging apparatus includes a data obtainer configured to obtain raw data generated by performing a tomography scan on an object. The medical imaging apparatus also includes a processor configured to obtain, from the raw data, a plurality of pieces of monochromatic image data respectively corresponding to a plurality of energy levels. The processor is also configured to receive an external input that sets a combination of weights respectively applied to the plurality of pieces of monochromatic image data. The processor is also configured to generate a synthetic image by applying the combination of the weights to the plurality of pieces of monochromatic image data. The medical imaging apparatus also includes a display configured to display the generated synthetic image.

The processor may be further configured to, when the combination of the weights respectively applied to the plurality of pieces of monochromatic image data is changed, generate the synthetic image by applying the changed combination of the weights.

The display may be further configured to display the combination of the weights respectively applied to the plurality of pieces of monochromatic image data by using a graph.

The processor may be further configured to change the combination of the weights in response to an external input that changes a shape of the graph.

The processor may be further configured to receive an external input that touches and drags the graph in a predetermined direction and change the shape of the graph based on the received external input.

The processor may be further configured to set two or more energy levels from among the plurality of energy levels to one group and set weights applied to two or more pieces of monochromatic image data corresponding to the one group from among the plurality of pieces of monochromatic image data to a same value.

The processor may be further configured to store the combination of the weights respectively applied to the plurality of pieces of monochromatic image data.

The processor may be further configured to generate the synthetic image by applying the stored combination of the weights to the plurality of pieces of monochromatic image data in response to an external input that selects the stored combination of the weights.

The processor may be further configured to obtain a plurality of pre-generated monochromatic images that are pre-generated as the plurality of pieces of monochromatic image data respectively corresponding to the plurality of energy levels.

According to an aspect of another embodiment, a method of processing a medical image includes obtaining raw data generated by performing a tomography scan on an object. The method also includes obtaining, from the raw data, a plurality of pieces of monochromatic image data respectively corresponding to a plurality of energy levels. The method also includes receiving an external input that sets a combination of weights respectively applied to the plurality of pieces of monochromatic image data; generating a synthetic image by applying the combination of the weights to the plurality of pieces of monochromatic image data; and displaying the generated synthetic image.

According to an aspect of another embodiment, a non-transitory computer-readable recording medium having embodied thereon computer program code for executing a method of processing a medical image when read and executed by a processor, the method including obtaining raw data generated by performing a tomography scan on an object. The method also includes obtaining, from the raw data, a plurality of pieces of monochromatic image data respectively corresponding to a plurality of energy levels. The method also includes generating a synthetic image of the object by respectively applying weights to the plurality of pieces of monochromatic image data. The method also includes displaying the generated synthetic image Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 4A and 4B illustrate views for explaining a process of updating a synthetic image as a combination of weights is changed, according to an embodiment;

FIGS. 6A through 6C illustrate views for explaining a process of setting two or more energy levels to one group and setting weights applied to two or more monochromatic images corresponding to the one group to a same value, according to an embodiment;

FIGS. 8A and 8B illustrate views for explaining a process of storing a combination of weights, according to an embodiment; and FIG. 9 illustrates a method of processing a medical image, according to an embodiment.

DETAILED DESCRIPTION

Figure 1:
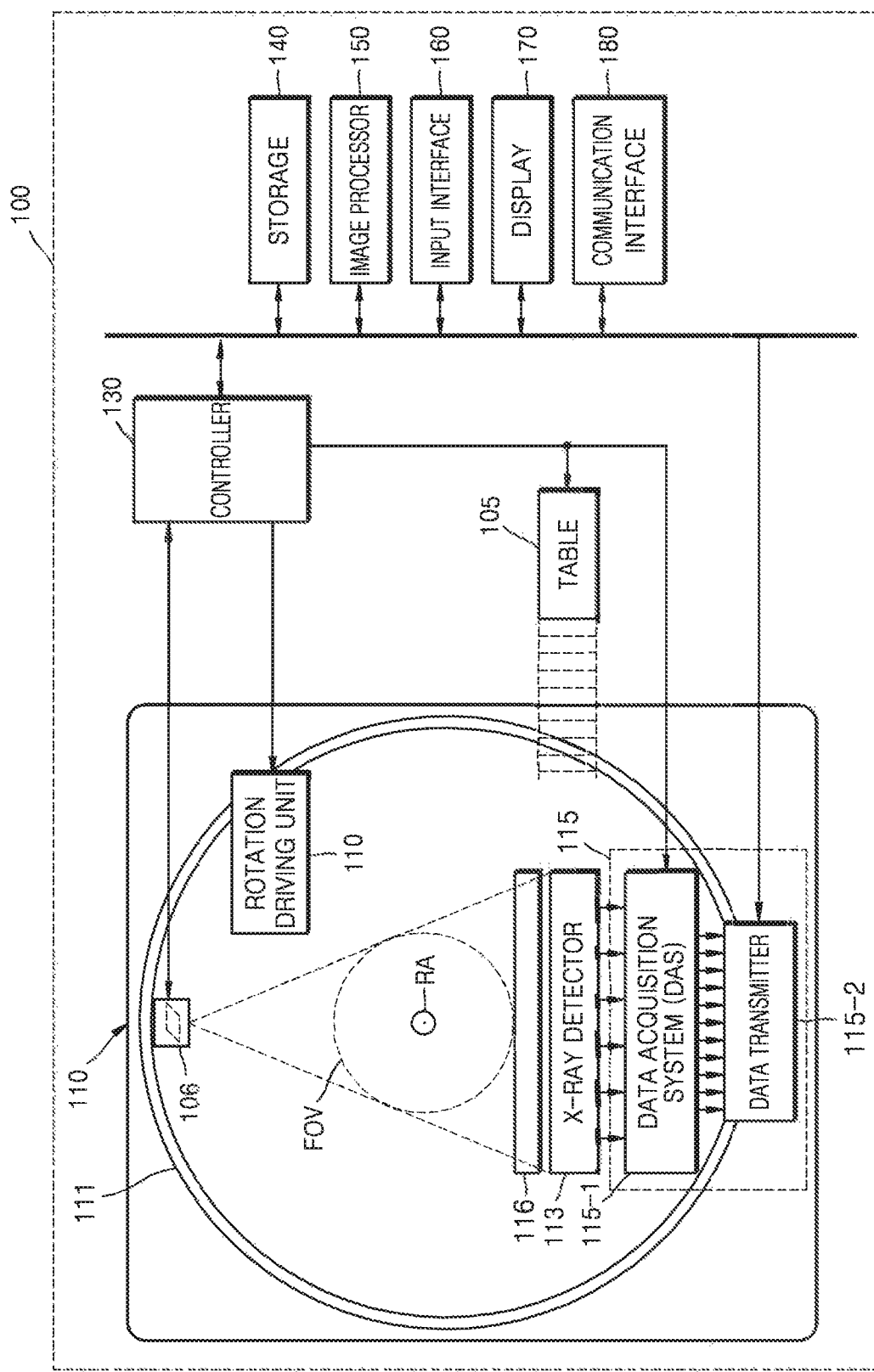
FIG. 1 illustrates a structure of a computed tomography (CT) system according to an embodiment.

FIGS. 1 through 9, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Throughout the specification, like reference numerals or characters refer to like elements. In the present specification, all elements of embodiments are not explained, but general matters in the technical field of the present disclosure or redundant matters between embodiments will not be described. Terms 'part' and 'portion' used herein may be implemented using software or hardware, and, according to embodiments, a plurality of 'parts' or 'portions' may be implemented using a single unit or element, or a single 'part' or 'portion' may be implemented using a plurality of units or elements. The operational principle of the present disclosure and embodiments thereof will now be described more fully with reference to the accompanying drawings.

In the present specification, an image may include a medical image obtained by a medical imaging apparatus such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and image the object by detecting the X-rays.

In the specification, a 'CT image' refers to an image constructed from raw data obtained by imaging an object by detecting X-rays that are emitted as the CT system or apparatus rotates about at least one axis with respect to the object.

Expressions such as "at least one of", when preceding a list of elements, modify the entire list of elements and do not modify the individual elements of the list.

FIG. 1 illustrates a structure of a CT system 100 according to an embodiment.

The CT system 100, according to an embodiment, may include a gantry 110, a table 105, a controller 130, a storage 140, an image processor 150, an input interface 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and may rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and current from a high voltage generator (HVG) to generate and emit X-rays.

The CT system 100 may be implemented as a single-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector (PCD), and the like.

Methods of driving the X-ray generator 112 and the X-ray detector 113 may vary depending on scan modes used to scan the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program code for performing a predetermined function or data and a processor configured to process the program code or the data. The controller 130 may include various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal to the data transmitter 115-2. The data transmitter 115-2 uses a circuit such as a multiplexer (MUX) to output the signal amplified by the DAS 115-1 to the image processor 150. According to a slice thickness or the number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomography image, to thereby generate the tomography data. According to an embodiment, the tomography data may be in the form of data that has undergone back-projection, or in the form of a tomography image. According to embodiments, additional processing may be performed on the tomography data by an external device such as a server, a medical apparatus, or a portable device.

The CT system 100 obtains raw data by performing a CT scan on the object in order to obtain a tomography image. The CT system 100 generates X-rays, emits the X-rays to the object, and detects X-rays passing through the object by using the X-ray detector 113. The X-ray detector 113 generates raw data corresponding to the detected X-rays. The raw data may refer to data before being reconstructed as a tomography image by the image processor 150. Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, and the like, and may include a volatile or non-volatile storage medium.

The input interface 160 receives control signals, data, and the like, from a user. The display 170 may display information indicating an operating status of the CT system 100, medical information, medical image data, and the like.

The CT system 100 includes the communication interface 180 and may be connected to external devices, such as a server, a medical apparatus, and a portable device (e.g., a smartphone, a tablet personal computer (PC), a wearable device, and the like), via the communication interface 180.

The communication interface 180 may include one or more components that enable communication with an external device. For example, the communication interface 180 may include at least one of a short distance communication module, a wired communication module, and a wireless communication module.

The communication interface 180 may receive control signals and data from an external device and may transmit the received control signals to the controller 130 such that the controller 130 may control the CT system 100 according to the received control signals.

Alternatively, by transmitting a control signal to an external device via the communication interface 180, the controller 130 may control the external device according to the control signal.

For example, the external device may process data according to a control signal received from the controller 130 via the communication interface 180.

A program for controlling the CT system 100 may be installed on the external device and may include instructions for performing some or all of the operations of the controller 130.

The program may be preinstalled on the external device, or a user of the external device may download the program from a server that provides an application for installation. The server that provides the application may include a recording medium having the program recorded thereon.

According to embodiments, the CT system 100 may or may not use contrast media during a CT scan, and may be implemented as a device connected to other equipment.

Figure 2:
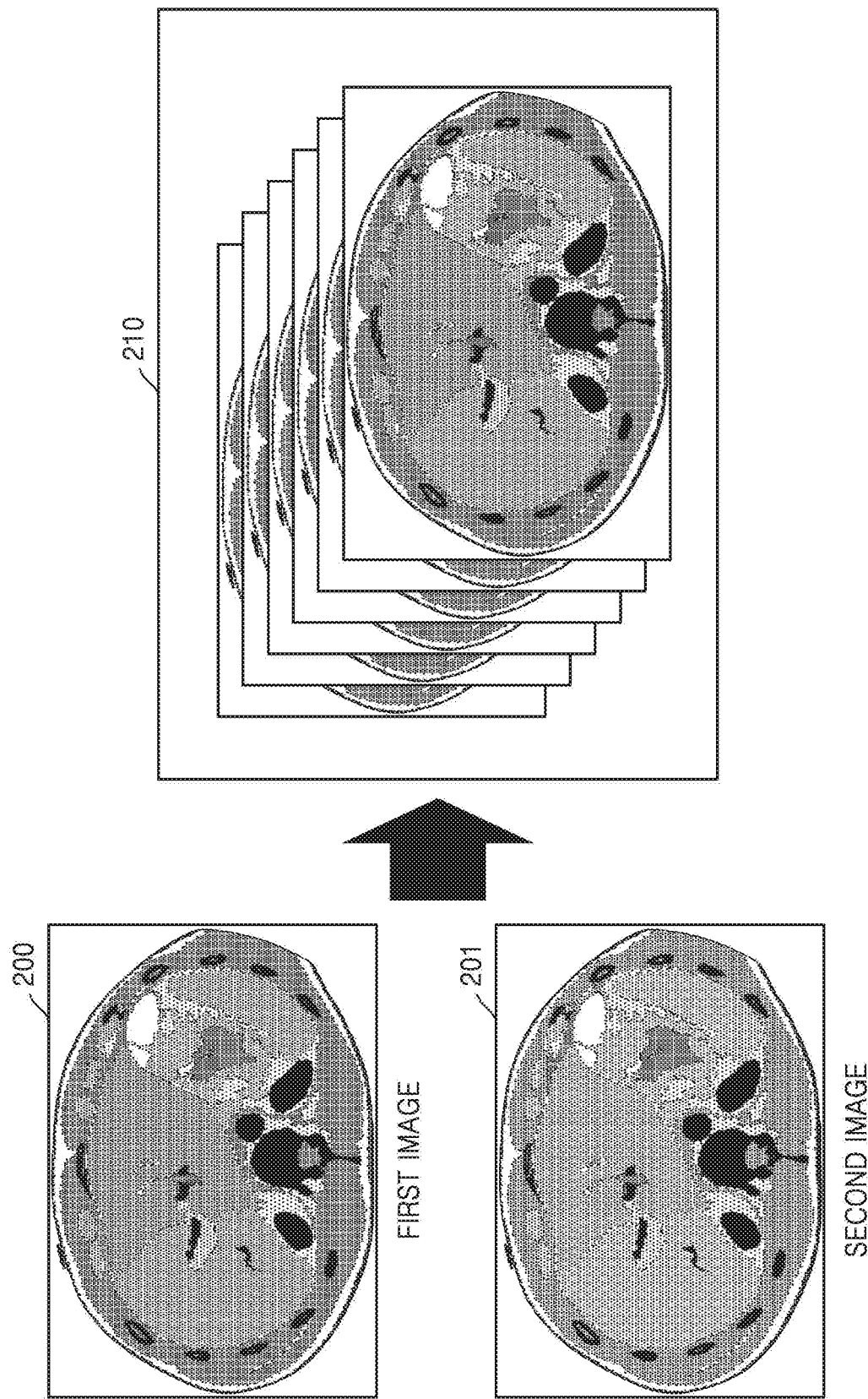
FIG. 2 illustrates a view for explaining a process of obtaining a plurality of monochromatic images respectively corresponding to a plurality of energy levels, according to an embodiment.

FIG. 2 illustrates a view for explaining a process of obtaining a plurality of monochromatic images respectively corresponding to a plurality of energy levels, according to an embodiment.

A medical imaging apparatus, according to an embodiment, may display a monochromatic image. The term 'monochromatic image' may refer to an image generated when a tomography scan is performed on an object by emitting X-rays having a monochromatic level. The monochromatic level corresponds to an energy level represented by a single value or a predetermined range of energy levels.

A brightness represented by a Hounsfield unit (HU) in a medical image may vary according to a linear attenuation coefficient of a material through which X-rays pass. The linear attenuation coefficient may vary according to an energy level of photons constituting the X-rays and a component of the material. Accordingly, even when a first material and a second material in the object are different from each other, linear attenuation coefficients may be similar to each other at a specific energy level. Accordingly, since the first material and the second material are displayed to have similar brightnesses, it may be difficult for a user to distinguish the first material from the second material. In this example embodiment, the user may clearly distinguish different materials by comparing monochromatic images corresponding to different energy levels (e.g., 50 keV and 100 keV).

According to an embodiment, the medical imaging apparatus images the object by emitting polychromatic X-rays including photons having various energy levels. According to an embodiment, the medical imaging apparatus may obtain monochromatic images respectively corresponding to a plurality of energy levels from raw data obtained by imaging the object by emitting polychromatic X-rays.

For example, the medical imaging apparatus may obtain first raw data and second raw data by performing a tomography scan by emitting X-rays having two different energy spectra to the object. For example, the medical imaging apparatus may obtain the first raw data and the second raw data by performing a tomography scan by emitting X-rays having tube voltages of 80 kVp and 140 kVp to the object. Once the first raw data and the second raw data are obtained, the medical imaging apparatus may reconstruct the first raw data and the second raw data and may obtain a first image 200 and a second image 201 that are monochromatic images corresponding to different energy levels.

Referring to FIG. 2, the medical imaging apparatus may obtain a plurality of monochromatic images 210 respectively corresponding to a plurality of energy levels based on the first image 200 and the second image 201. For example, the medical imaging apparatus may obtain the plurality of monochromatic images 210 respectively corresponding to the plurality of energy levels by applying a virtual monochromatic imaging method to the first image 200 and the second image 201. For example, the medical imaging apparatus may obtain a plurality of monochromatic images respectively corresponding to 20 energy levels that are sampled in an energy band equal to or greater than 40 keV and equal to or less than 140 keV. For example, the plurality of monochromatic images may be monochromatic images respectively corresponding to a plurality of energy levels that are sampled at intervals of 5 keV in the energy band equal to or greater than 40 keV and equal to or less than 140 keV.

According to another embodiment, the medical imaging apparatus may obtain a plurality of monochromatic images respectively corresponding to a plurality of energy levels by using a PCD. For example, the medical imaging apparatus may obtain a plurality of monochromatic images by detecting photons respectively corresponding to a plurality of energy levels. According to a structure of the PCD, photons having a plurality of energy levels may be detected by imaging the object multiple times according to the plurality of energy levels or photons having a plurality of energy levels may be detected by imaging the object one time.

Figure 3:
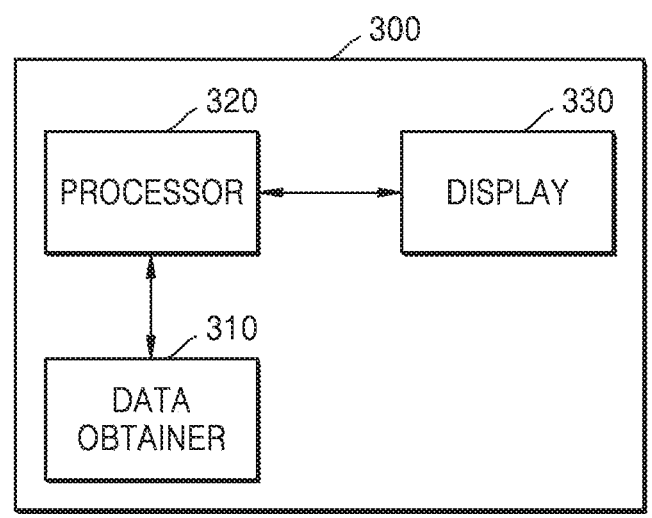
FIG. 3 illustrates a block diagram of a configuration of a medical imaging apparatus according to an embodiment.

FIG. 3 illustrates a block diagram of a configuration of a medical imaging apparatus 300 according to an embodiment.

The medical imaging apparatus 300, according to one or more embodiments, is an apparatus for processing and displaying medical image data may be implemented as an electronic apparatus. For example, the medical imaging apparatus 300 may be implemented as any of various apparatuses including a processor and a display such as a general-purpose computer, a tablet PC, or a smartphone.

The medical imaging apparatus 300, according to embodiments, may be implemented in the form of the CT system 100 of FIG. 1.

Referring to FIG. 3, the medical imaging apparatus 300, according to an embodiment, may include a data obtainer 310, a processor 320, and a display 330. However, embodiments are not limited thereto, and the medical imaging apparatus 300 may include elements more than those illustrated in FIG. 3.

The elements will now be explained.

The data obtainer 310 according to an embodiment may obtain raw data generated by performing a tomography scan on an object. The raw data may be obtained by using any of various methods. For example, the raw data may be obtained from a scanner of the medical imaging apparatus 300 or may be received from an external device.

According to an embodiment, the data obtainer 310 may correspond to the scanner of the medical imaging apparatus 300 and may include, for example, the gantry 110 of the CT system 100 of FIG. 1. Accordingly, the data obtainer 310 may include the rotating frame 111, the X-ray generator 112, the X-ray detector 113, the rotation driver 114, and the readout device 115 of FIG. 1.

According to an embodiment, the data obtainer 310 may obtain first raw data and second raw data by performing a tomography scan by emitting X-rays having two different energy spectra to an object. For example, the data obtainer 310 may obtain the first raw data and the second raw data by, but not limited to, performing a tomography scan by emitting X-rays having a tube voltage of 80 kVp to the object and performing a tomography scan by emitting X-rays having a tube voltage of 140 kVp to the object. Imaging using the X-rays having the tube voltages of 80 kVp and 140 kVp may be performed one time or two times according to a structure of the scanner.

According to another embodiment, the data obtainer 310 may be implemented as a communication interface that communicates with the external device. The data obtainer 310 may receive raw data obtained by imaging the object from the external device.

The processor 320 may perform predetermined processing based on a received user input. The processor 320 may include various combinations of at least one memory and at least one processor. For example, the memory may generate and delete a program module according to an operation of the processor 320 and the processor 320 may process operations of the program module.

The processor 320, according to an embodiment, obtains a plurality of pieces of monochromatic image data respectively corresponding to a plurality of energy levels from the raw data obtained by the data obtainer 310.

The plurality of pieces of monochromatic image data may include one or more pixel values of a plurality of monochromatic images or the plurality of monochromatic images. For example, when the one or more pixel values of the plurality of monochromatic images are obtained as the plurality of pieces of monochromatic image data, the processor 320 may calculate the one or more pixel values of the plurality of monochromatic images from the raw data obtained by the data obtainer 310. Also, the processor 320 may generate a synthetic image by applying a combination of weights to the one or more pixel values of the plurality of monochromatic images. Accordingly, the processor 320 may reduce the amount of calculation used to generate the plurality of monochromatic images from the one or more pixel values of the plurality of monochromatic images.

The processor 320, according to an embodiment, may generate the plurality of pieces of monochromatic image data from the obtained raw data or may receive the plurality of pieces of monochromatic image data that are pre-generated from the outside. However, embodiments are not limited thereto. For example, the processor 320 may obtain the plurality of pieces of monochromatic image data respectively corresponding to 20 energy levels that are sampled in an energy band equal to or greater than 40 keV and equal to or less than 140 keV. For example, the 20 energy levels may be energy levels that are sampled at intervals of 5 keV in the energy band equal to or greater than 40 keV and equal to or less than 140 keV. However, embodiments are not limited thereto, and a range of an energy band in which the plurality of pieces of monochromatic image data are obtained and sampling intervals may be changed.

The processor 320 according to an embodiment may receive an external input that sets a combination of weights respectively applied to the plurality of pieces of monochromatic image data. Also, the processor 320 may generate a synthetic image by applying the combination of the weights respectively set to the plurality of pieces of monochromatic image data.

For example, the processor 320 may apply different weights to 20 pieces of monochromatic image data. For example, the processor 320 may apply a greater weight to monochromatic image data corresponding to an energy level at which a lesion or a material to be observed by a user is easily checked than to monochromatic image data corresponding to other energy levels. Accordingly, the generated synthetic image may more clearly show the lesion or the material to be observed by the user. Accordingly, the user may easily interpret the lesion or the material in the object by using one synthetic image without checking the plurality of monochromatic images.

In response to an input that changes the combination of the weights respectively applied to the plurality of pieces of monochromatic image data, the processor 320 according to an embodiment may update the synthetic image by applying the changed combination of the weights. For example, the input that changes the combination of the weights may include, but is not limited to, an input that changes a shape of a graph showing the combination of the weights or an input that directly changes values of the weights.

The display 330, according to an embodiment, may display a medical image obtained by performing a tomography scan on the object.

When the display 330 is implemented as a touchscreen, the display 330 may be used as an input device as well as an output device. The display 330 may be, for example, a liquid crystal display, a thin-film transistor liquid crystal display, an organic light-emitting diode, a flexible display, a three-dimensional (3D) display, or an electrophoretic display. Also, according to a type of the medical imaging apparatus 300, the medical imaging apparatus 300 may include two or more displays 330.

The display 330, according to an embodiment, displays the synthetic image generated by the processor 320.

Also, the display 330, according to an embodiment, may display the combination of the weights respectively applied to the plurality of pieces of monochromatic image data by using at least one of a graph and numbers. For convenience of explanation, the following will be explained on the assumption that the plurality of pieces of monochromatic image data are a plurality of monochromatic images.

FIGS. 4A and 4B illustrate views for explaining a method of processing a medical image according to an embodiment.

The medical imaging apparatus 300, according to an embodiment, may generate a synthetic image by respectively applying weights to a plurality of monochromatic images.

When the plurality of monochromatic images are images respectively corresponding to energy levels that are sampled at intervals of 5 keV in an energy band equal to or greater than 40 keV and equal to or less than 140 keV, the medical imaging apparatus 300 may obtain 20 monochromatic images.

The medical imaging apparatus 300, according to an embodiment, may respectively apply weights to a plurality of monochromatic images. For example, the medical imaging apparatus 300 may respectively apply different weights to the plurality of monochromatic images. The medical imaging apparatus 300 may apply a greater weight to a monochromatic image corresponding to an energy level at which a lesion or a material to be observed by a user may be easily interpreted than to monochromatic images corresponding to other energy levels. For example, an energy level at which iodine in an object may be easily interpreted may be an energy level equal to or greater than 65 keV and equal to or less than 75 keV. In this example embodiment, the medical imaging apparatus 300 may generate a synthetic image by applying a greater weight to a monochromatic image corresponding to the energy level equal to or greater than 65 keV and equal to or less than 75 keV than to other monochromatic images. For example, the medical imaging apparatus 300 may set a weight of the monochromatic image corresponding to the energy level equal to or greater than 65 keV and equal to or less than 75 keV to 100 and may set weights of other monochromatic images to 0.

The medical imaging apparatus 300, according to an embodiment, may generate a synthetic image 400 by applying a combination of weights respectively set to the 20 monochromatic images. In this example embodiment, the generated synthetic image 400 may more clearly show iodine in the object. Accordingly, the user may more easily check iodine in the object by using the synthetic image 400.

The medical imaging apparatus 300, according to an embodiment, may display the combination of the weights respectively applied to the plurality of monochromatic images by using at least one of a graph and numbers.

For example, referring to FIG. 4A, the medical imaging apparatus 300 may display the combination of the weights respectively applied to the 20 monochromatic images by using a graph 401. In this example embodiment, the x-axis of the graph 401 may represent an energy level, and the y-axis of the graph 401 may represent a weight applied to a monochromatic image corresponding to each energy level. For example, the weight may have a value equal to or greater than 0 and equal to or less than 100. However, embodiments are not limited thereto, and a range of the weight may vary according to embodiments. The medical imaging apparatus 300 may display the combination of the weights by using the graph 401 such that the user may intuitively check the combination of the weights respectively applied to the plurality of monochromatic images.

Alternatively, as shown in FIG. 4A, the medical imaging apparatus 300 may display the combination of the weights respectively applied to the 20 monochromatic images by using numbers 402.

As the combination of the weights respectively applied to the plurality of monochromatic images is changed, the medical imaging apparatus 300 according to an embodiment may update the synthetic image 400 by applying the changed combination of the weights. In this example embodiment, the medical imaging apparatus 300 may change the combination of the weights in response to an external input that changes a shape of a graph. For example, referring to FIG. 4B, the user may change the combination of the weights by moving an indicator 420 to a desired location on a graph 421. The user may change a location of the indicator 420 by using an input that touches and drags the indicator 420 or by using a mouse. For example, the medical imaging apparatus 300 may receive an input that touches and drags the indicator 420 in a predetermined direction on the graph 421 and may change a location of the indicator 420 based on the received input. The medical imaging apparatus 300 may change a shape of a graph to correspond to the changed location of the indicator 420 and may change the combination of the weights to correspond to the changed shape of the graph. Also, in response to an input that changes a shape of the graph 401 of FIG. 4A into a shape of the graph 421 of FIG. 4B, the medical imaging apparatus 300 may automatically change values 422 indicating the combination of the weights to correspond to the changed graph 421.

The medical imaging apparatus 300, according to an embodiment, may generate a synthetic image by applying the changed combination of the weights. For example, as the combination of the weights is changed, the medical imaging apparatus 300 may automatically update and display a synthetic image to which the changed combination of the weights is applied. A synthetic image 410 of FIG. 4B may more clearly show a material 411 located at a predetermined position in the object than the synthetic image 400 of FIG. 4A. Accordingly, the user may check an energy level at which a lesion or a material to observed by the user is more clearly shown, and may apply a relatively great weight to a monochromatic image corresponding to the energy level. The user may more easily interpret the lesion or the material to be observed by using the generated synthetic image.

Figure 5:
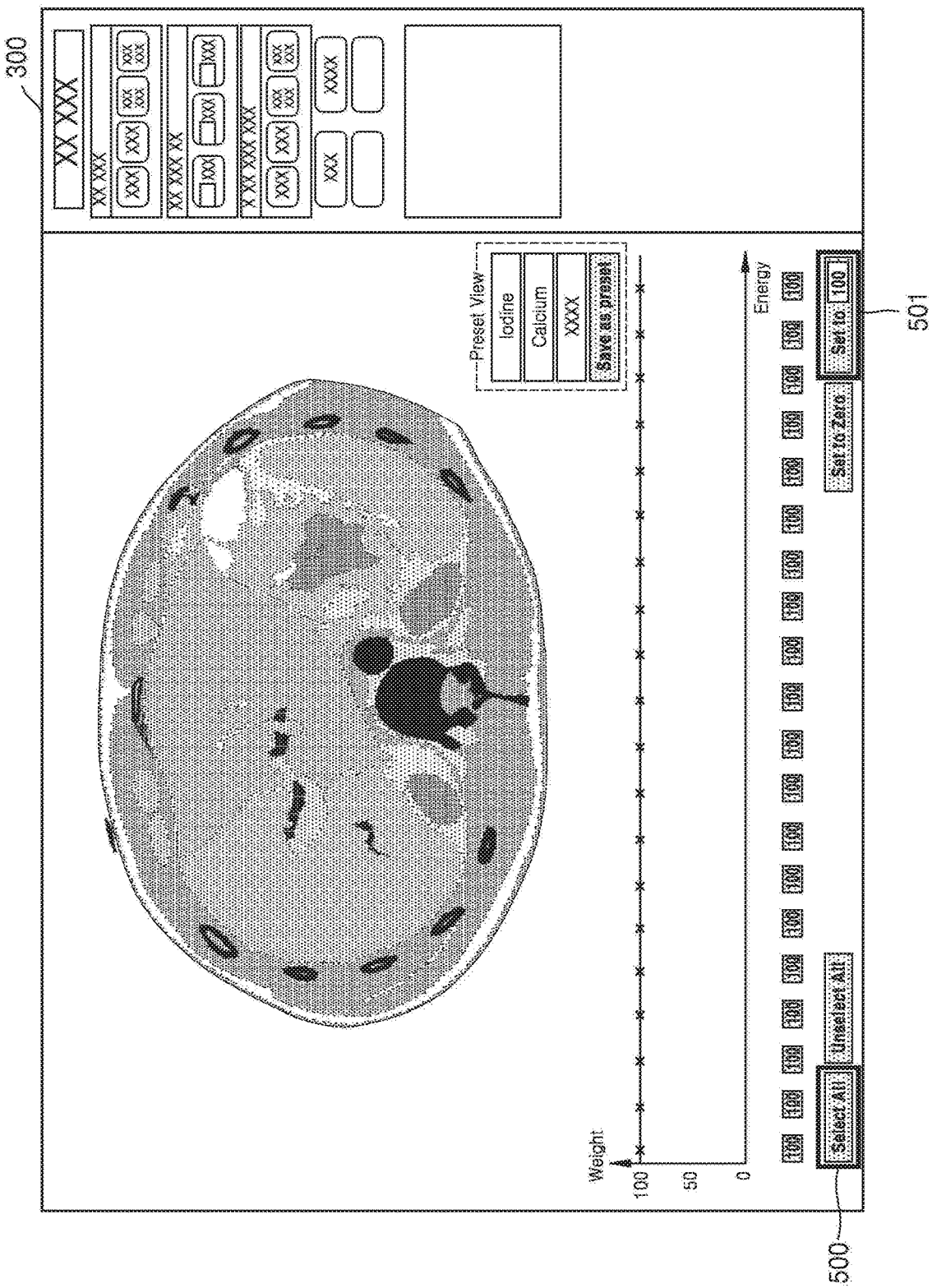
FIG. 5 illustrates a view for explaining a process of setting weights respectively applied to a plurality of monochromatic images to a same value, according to an embodiment.

FIG. 5 illustrates a view for explaining a process of setting weights respectively applied to a plurality of monochromatic images to the same value according to an embodiment.

The medical imaging apparatus 300, according to an embodiment, may set weights respectively applied to a plurality of monochromatic images to the same value.

For example, referring to FIG. 5, the medical imaging apparatus 300 may receive an input that sets all weights of 20 monochromatic images to 100. In this example embodiment, the medical imaging apparatus 300 may additionally provide a user interface for selecting all energy bands such that a user may easily set weights. For example, the input that selects all energy bands may be, but is not limited to, an input that clicks on or touches a menu "Select All" 500 displayed on a display, as shown in FIG. 5. Once all energy bands are selected, the medical imaging apparatus 300 may set weights of all monochromatic images to the same value in response to an input 501 that sets values of weights. Also, the medical imaging apparatus 300 may generate a synthetic image by applying the weights set to the same value to all monochromatic images.

Figure 6A:
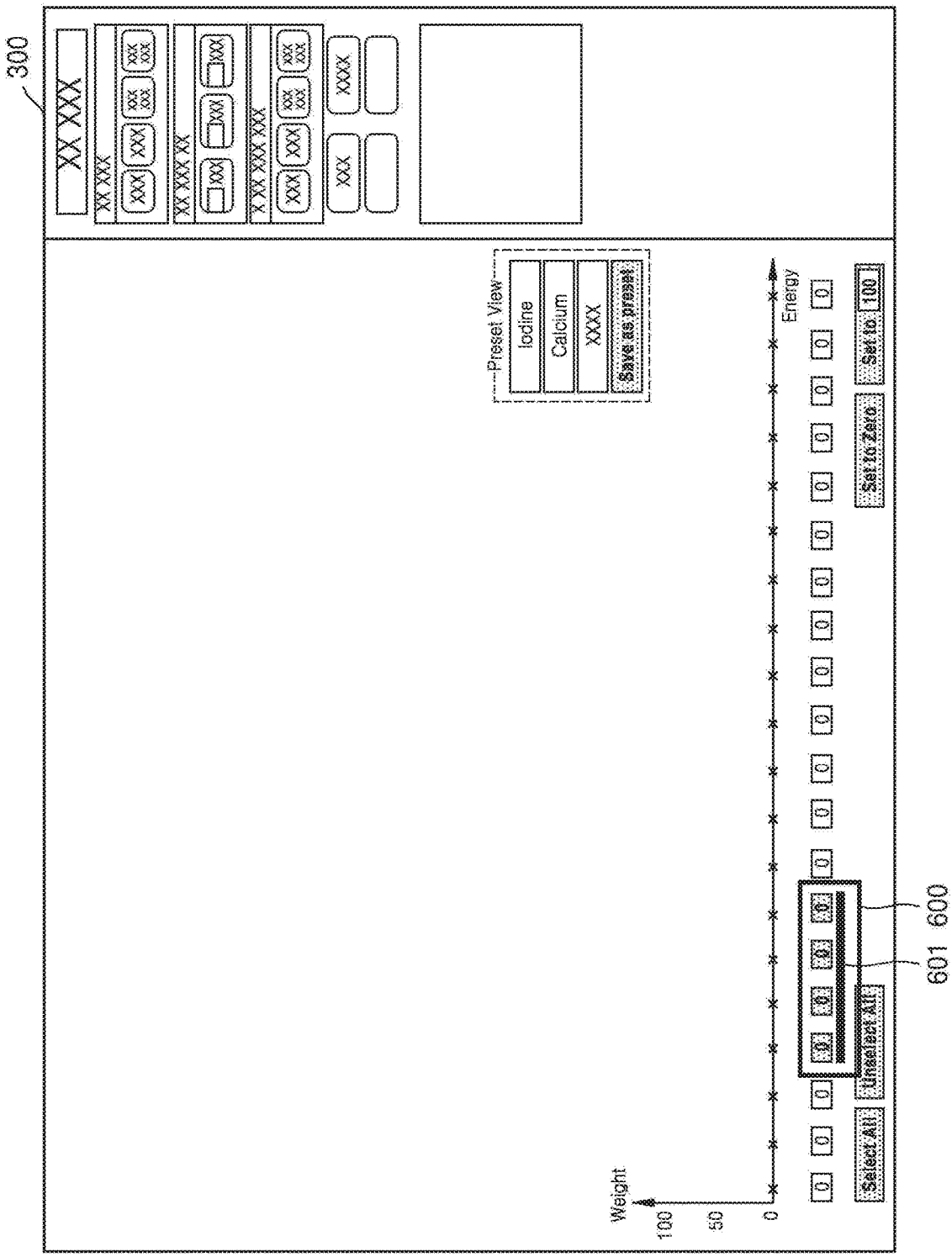

FIGS. 6A through 6C illustrate views for explaining a process of setting two or more energy levels to one group and setting weights applied to two or more monochromatic images corresponding to the one group to the same value according to an embodiment.

The medical imaging apparatus 300, according to an embodiment, may set two or more energy levels to one group. For example, referring to FIG. 6A, the medical imaging apparatus 300 may set a fourth energy level through a seventh energy level to one group 600. For example, when a plurality of monochromatic images are images corresponding to energy levels that are sampled at intervals of 5 keV in an energy band equal to or greater than 40 keV and equal to or less than 140 keV, an energy band set to the group 600 may be an energy band equal to or greater than 55 keV and equal to or less than 70 keV.

The medical imaging apparatus 300, according to an embodiment, may display a plurality of energy levels set to one group such that the plurality of energy levels are distinguished from one another. For example, referring to FIG. 6A, the medical imaging apparatus 300 may display that the fourth energy level through the seventh energy level are set to the group 600 by using an indicator 601 such as a bar. The medical imaging apparatus 300 according to another embodiment may display the fourth energy level through the seventh energy level set to the group 600 by using, but not limited to, highlighting or text.

The medical imaging apparatus 300, according to an embodiment, may set two or more energy levels to one group and may apply the same weight to two or more monochromatic images corresponding to the group. Accordingly, the medical imaging apparatus 300 may enable a user to more easily set a weight of a specific energy band. For example, referring to FIG. 6B, the medical imaging apparatus 300 may receive a user input that sets weights of two more monochromatic images corresponding to a set group to 100. The input that sets the weights to 100 may include, but is not limited to, an input 610 that directly sets a value by using a keyboard or a numeric keypad or an input that moves an indicator 612 displayed on a graph. For example, when the user directly inputs a value of weights applied to a set group, the medical imaging apparatus 300 may automatically change a shape 611 of a graph showing a combination of the weights to correspond to the user input.

When the combination of the weights is changed, the medical imaging apparatus 300 according to an embodiment may update a synthetic image in real time by applying the changed combination of the weights. For example, referring to FIG. 6B, the medical imaging apparatus 300 may generate and display a synthetic image 620 to which the changed combination of the weights is applied.

The medical imaging apparatus 300, according to an embodiment, may change a location of an energy band set to one group. For example, referring to FIG. 6C, in response to an input that moves an indicator 640 indicating a set group, the medical imaging apparatus 300 may change a location of a group from the energy band equal to or greater than 55 keV and equal to or less than 70 keV to an energy band equal to or greater than 100 keV and equal to or less than 115 keV. Accordingly, the energy band equal to or greater than 100 keV and equal to or less than 115 keV may be set to one group. As an energy band set to a group is changed, a combination of weights applied to a plurality of monochromatic images is also changed.

As the combination of the weights is changed, the medical imaging apparatus 300 according to an embodiment may update in real time a synthetic image generated by applying the changed combination of the weights. Accordingly, the medical imaging apparatus 300 may enable the user to more easily check a synthetic image to which a combination of specific weights is applied and may more easily set a combination of weights for obtaining a synthetic image desired by the user.

Figure 7:
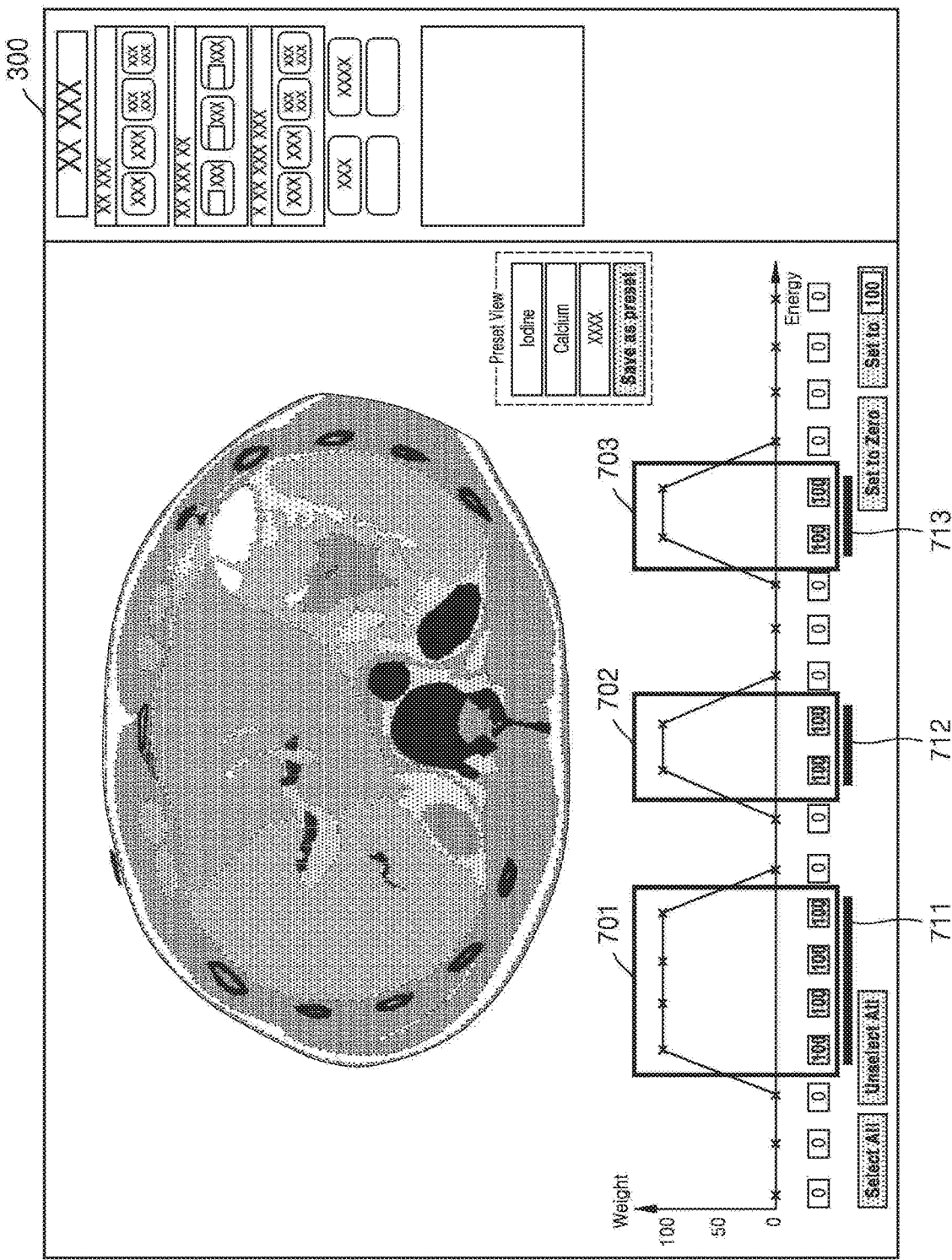
FIG. 7 illustrates a view for explaining a process of setting a plurality of groups, according to an embodiment.

FIG. 7 illustrates a view for explaining a process of setting a plurality of groups according to an embodiment.

A user may set two or more groups each including two or more energy levels. For example, referring to FIG. 7, the user may set a $4^{th}$ energy level through a $7^{th}$ energy level (e.g., energy levels equal to or greater than 55 keV and equal to or less than 70 keV) from among 20 energy levels to a first group 701, a $10^{th}$ energy level and an $11^{th}$ energy level (e.g., 85 keV and 90 keV) to a second group 702, and a $16^{th}$ energy level and $17^{th}$ energy level (e.g., 110 keV and 115 keV) to a third group 703. Also, the user may set the same weight to two or more monochromatic images corresponding to each group.

The medical imaging apparatus 300, according to an embodiment, may display a plurality of groups such that the plurality of groups is distinguished from one another. For example, the medical imaging apparatus 300 may distinguishably display the plurality of groups by using different colors or text. Alternatively, as shown in FIG. 7, the medical imaging apparatus 300 may display, but is not limited to, indicators 711, 712, and 713 respectively indicating the first through groups 701, 702, and 703.

Figure 8B:
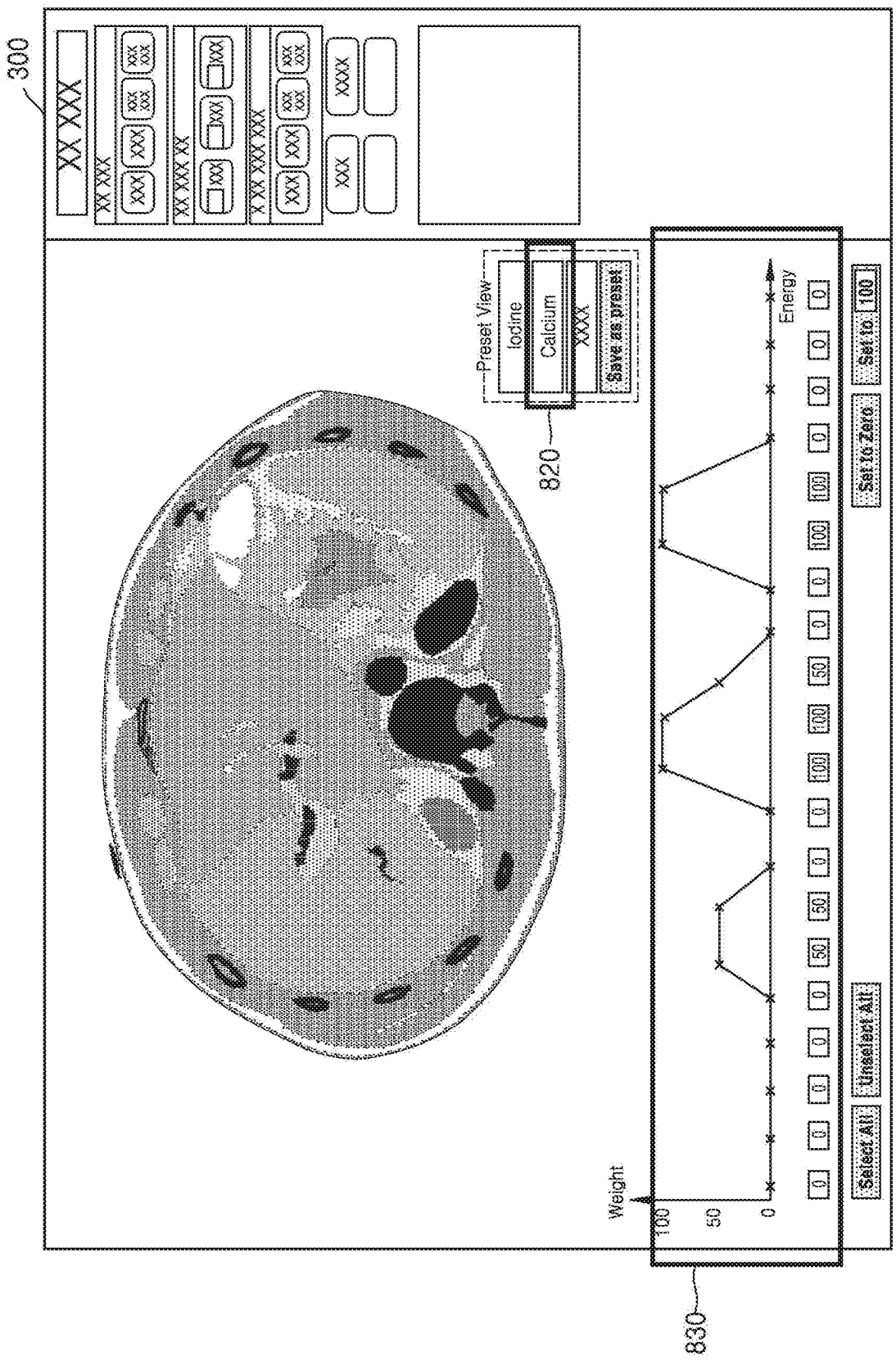

FIGS. 8A and 8B illustrate views for explaining a process of storing a combination of weights according to an embodiment.

The medical imaging apparatus 300, according to an embodiment, may store a combination of weights applied to a plurality of monochromatic images. For example, when a combination of specific weights is often used, it may be inconvenient for a user to set a combination of weights whenever necessary. Alternatively, when it is determined that a combination of specific weights is suitable to interpret a specific lesion or a specific material, the user may store the combination of the specific weights and may use the stored combination of the specific weights whenever necessary.

For example, a synthetic image generated by applying a combination 800 of weights of FIG. 8A may be an image with which calcium in an object may be easily detected. In this example embodiment, the medical imaging apparatus 300 may store the combination 800 of the weights of FIG. 8A. In this example embodiment, the medical imaging apparatus 300 may provide an additional user interface for storing the combination 800 of the weights. For example, the medical imaging apparatus 300 may display a menu "SAVE" 810 on the display 330 as shown in FIG. 8A. The user may store the combination 800 of the weights of FIG. 8A by, but not limited to, touching or clicking on the menu "SAVE" 810.

When a combination of specific weights is stored, the medical imaging apparatus 300 according to an embodiment may also set a name for identifying the combination of the weights such that the user may easily identify the combination of the weights that is stored. For example, the medical imaging apparatus 300 may store a name of the combination 800 of the weights of FIG. 8A as "Calcium".

The medical imaging apparatus 300, according to an embodiment, may display a user interface for selecting the stored combination of the weights on the display 330 such that the user may easily select the stored combination of the weights. For example, as shown in FIG. 8B, the medical imaging apparatus 300 may display an icon 820 indicating the stored combination of the weights on the display 330. The user may select the stored combination 800 of the weights by clicking on or touch the displayed icon 820. However, the user interface for selecting the stored combination of the weights is not limited thereto, and may vary according to embodiments.

The medical imaging apparatus 300, according to an embodiment, may generate a synthetic image by applying the selected combination 800 of the weights. For example, when calcium existing in the object is to be detected, in response to a user input that selects the icon 820, the medical imaging apparatus 300 may display the combination of the weights stored as "Calcium" on the display 330. The medical imaging apparatus 300 may generate a synthetic image by applying the combination of the weights stored as "Calcium" to a plurality of monochromatic images.

FIG. 9 illustrates a method of processing a medical image according to an embodiment.

Operations of a method of processing a medical image, according to embodiments, may be performed by an electronic apparatus including a processor for processing an image and a display. The following will be explained on the assumption that the medical imaging apparatus 300 performs the method. Accordingly, the description given for the medical imaging apparatus 300 may be applied to the method, and conversely, the description given for the method may be applied to the medical imaging apparatus 300. Although the method according to embodiments is performed by the medical imaging apparatus 300, embodiments are not limited thereto, and the method may be performed by various other electronic apparatuses.

In operation S910, the medical imaging apparatus 300 obtains raw data by performing a tomography scan on an object.

For example, the medical imaging apparatus 300 may obtain first raw data and second raw data by performing a tomography scan by emitting X-rays having two different energy spectra to the object.

In operation S920, the medical imaging apparatus 300 obtains a plurality of pieces of monochromatic image data respectively corresponding to a plurality of energy levels from the raw data.

As described above, the plurality of pieces of monochromatic image data may include one or more pixel values of a plurality of monochromatic images or the plurality of monochromatic images. For example, when the one or more pixel values of the plurality of monochromatic images are obtained as the plurality of pieces of monochromatic image data, the medical imaging apparatus 300 may calculate the one or more pixel values of the plurality of monochromatic images from the obtained raw data. The medical imaging apparatus 300 may generate a synthetic image by applying a combination of weights to the one or more pixel values of the plurality of monochromatic images.

For example, when a virtual monochromatic imaging method is used, the medical imaging apparatus 300 may obtain a first image and a second image by reconstructing the first raw data and the second raw data. Also, the medical imaging apparatus 300 may obtain a plurality of monochromatic images respectively corresponding to a plurality of energy levels based on the first image and the second image. Alternatively, according to embodiments, the medical imaging apparatus 300 may obtain the plurality of monochromatic images by using, but not limited to, a PCD.

In operation S930, the medical imaging apparatus 300 receives an external input that sets a combination of weights respectively applied to the plurality of pieces of monochromatic image data.

For example, the medical imaging apparatus 300 may set different weights to the plurality of pieces of monochromatic image data. For example, the medical imaging apparatus 300 may apply a greater weight to monochromatic image data corresponding to an energy level at which a lesion or a material to be observed by a user is easily checked than to monochromatic image data corresponding to other energy levels.

In operation S940, the medical imaging apparatus 300 generates a synthetic image by applying the combination of the weights to the plurality of pieces of monochromatic image data.

The generated synthetic image may more clearly show the lesion or the material to be observed by the user. Accordingly, the user may easily interpret a specific lesion or a specific material in the object by using one synthetic image, without checking the plurality of monochromatic images.

In response to an input that changes the combination of the weights, the medical imaging apparatus 300 may generate the synthetic image by applying the changed combination of the eights. For example, the input that changes the combination of the weights may include an input that changes a shape of a graph showing the combination of the weights. Alternatively, the input that changes the combination of the weights may include an input that directly changes values of the weights.

In operation S950, the medical imaging apparatus 300 displays the generated synthetic image.

For example, the medical imaging apparatus 300 may display the combination of the weights applied to the plurality of pieces of monochromatic image data by using at least one of a graph and numbers. Also, in response to a user input that changes the combination of the weights, the medical imaging apparatus 300 may display the synthetic image to which the changed combination of the weights is applied.

The above-described embodiments may be embodied in the form of a computer-readable recording medium for storing computer executable command languages and data. The command languages may be stored in the form of program code and, when executed by a processor, may perform a certain operation by generating a certain program module. Also, when executed by the processor, the command languages may perform certain operations of the disclosed embodiments.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A medical imaging apparatus comprising:
   a tomographic scanner configured to obtain raw data generated by performing a tomography scan on an object;
   a processor configured to:
   obtain, from the raw data, a plurality of pieces of monochromatic image data respectively corresponding to a plurality of energy levels,
   receive an external input by a user that selects at least one energy level among the plurality of energy levels and sets a combination of weights for the selected at least one energy level, and
   generate a synthetic image of the object by applying the combination of the weights for the at least one energy level to the plurality of pieces of monochromatic image data; and
   a display configured to display the combination of the weights applied to the plurality of pieces of monochromatic image data by using a graph and the generated synthetic image,
   wherein the processor is further configured to change the combination of the weights in response to an external input that changes a shape of the graph.

2. The medical imaging apparatus of claim 1, wherein the processor is further configured to, when the combination of the weights respectively applied to the plurality of pieces of monochromatic image data is changed, generate the synthetic image by applying the changed combination of the weights.

3. The medical imaging apparatus of claim 1, wherein the processor is further configured to receive an external input that touches and drags the graph in a predetermined direction and change the shape of the graph based on the received external input.

4. The medical imaging apparatus of claim 1, wherein the processor is further configured to set two or more energy levels from among the plurality of energy levels to one group and set weights applied to two or more pieces of monochromatic image data corresponding to the one group from among the plurality of pieces of monochromatic image data to a same value.

5. The medical imaging apparatus of claim 1, wherein the processor is further configured to store the combination of the weights respectively applied to the plurality of pieces of monochromatic image data.

6. The medical imaging apparatus of claim 5, wherein the processor is further configured to generate the synthetic image by applying the stored combination of the weights to the plurality of pieces of monochromatic image data in response to an external input that selects the stored combination of the weights.

7. The medical imaging apparatus of claim 1, wherein the processor is further configured to obtain a plurality of pre-generated monochromatic images as the plurality of pieces of monochromatic image data respectively corresponding to the plurality of energy levels.

8. A method of processing a medical image, the method comprising:
   obtaining raw data generated by performing a tomography scan on an object;
   obtaining, from the raw data, a plurality of pieces of monochromatic image data respectively corresponding to a plurality of energy levels;
   receiving an external input by a user that selects at least one energy level among the plurality of energy levels and sets a combination of weights for the selected at least one energy level;
   generating a synthetic image of the object by applying the combination of the weights for the at least one energy level to the plurality of pieces of monochromatic image data;
   displaying the combination of the weights applied to the plurality of pieces of monochromatic image data by using a graph and the generated synthetic image; and
   changing the combination of the weights in response to an external input that changes a shape of the graph.

9. The method of claim 8, wherein generating the synthetic image comprises, when the combination of the weights respectively applied to the plurality of pieces of monochromatic image data is changed, generating the synthetic image by applying the changed combination of the weights.

10. The method of claim 8, wherein changing the combination of the weights comprises:
receiving an external input that touches and drags the graph in a predetermined direction; and
changing the shape of the graph based on the received external input.

11. The method of claim 8, further comprising:
setting two or more energy levels from among the plurality of energy levels to one group; and
setting weights applied to two or more pieces of monochromatic image data corresponding to the one group from among the plurality of pieces of monochromatic image data to a same value.

12. The method of claim 8, further comprising storing the combination of the weights respectively applied to the plurality of pieces of monochromatic image data.

13. The method of claim 12, wherein generating the synthetic image comprises generating the synthetic image by applying the stored combination of the weights to the plurality of pieces of monochromatic image data in response to an external input that selects the stored combination of the weights.

14. The method of claim 8, wherein obtaining the plurality of pieces of monochromatic image data comprises obtaining a plurality of pre-generated monochromatic images as the plurality of pieces of monochromatic image data respectively corresponding to the plurality of energy levels.

15. A non-transitory computer-readable recording medium having embodied thereon computer program code for executing a method of processing a medical image when read and executed by a processor, the method comprising:
obtaining raw data generated by performing a tomography scan on an object;
obtaining, from the raw data, a plurality of pieces of monochromatic image data respectively corresponding to a plurality of energy levels;
receiving an external input by a user that selects at least one energy level among the plurality of energy levels and sets a combination of weights for the selected at least one energy level;
generating a synthetic image of the object by applying the combination of the weights for the at least one energy level to the plurality of pieces of monochromatic image data;
displaying the combination of the weights applied to the plurality of pieces of monochromatic image data by using a graph and the generated synthetic image; and
changing the combination of the weights in response to an external input that changes a shape of the graph.

\* \* \* \* \*